United States Patent
Pregenzer et al.

(10) Patent No.: US 6,372,006 B1
(45) Date of Patent: Apr. 16, 2002

(54) SEPARATOR ELEMENT FOR A CENTRIFUGAL SEPARATOR

(76) Inventors: Bruno Pregenzer, Untermieming 45a A-6414, Mieming; Alfred Konzett, Dorfstrasse 21a A-6082, Patsch, both of (AT)

( * ) Notice: Subject to any disclaimer, the term of this patent is extended or adjusted under 35 U.S.C. 154(b) by 0 days.

(21) Appl. No.: 09/547,685

(22) Filed: Apr. 12, 2000

(30) Foreign Application Priority Data

Apr. 12, 1999 (DE) ..................... 299 06 470 U

(51) Int. Cl.⁷ ................. B01D 45/14; A61C 17/14
(52) U.S. Cl. ............... 55/406; 96/196; 96/214; 96/216; 210/188; 210/512.1; 210/512.3; 433/92
(58) Field of Search .............. 96/194, 195, 196, 96/208, 214, 216; 55/406, 408; 433/92; 210/188, 512.1, 512.3

(56) References Cited

U.S. PATENT DOCUMENTS

| | | | |
|---|---|---|---|
| 2,593,294 A | * 4/1952 | Goldberg | 55/406 |
| 4,563,198 A | * 1/1986 | Houtchens | 55/192 |
| 4,844,691 A | * 7/1989 | Hallman et al. | 55/409 |
| 5,330,641 A | * 7/1994 | Cattani | 96/195 |
| 5,693,221 A | * 12/1997 | Ellinghaus | 96/195 |

FOREIGN PATENT DOCUMENTS

| | | | |
|---|---|---|---|
| EP | 0 680 289 B1 | 11/1995 | |
| EP | 0 726 744 B1 | 8/1996 | |
| WO | WO 94/18903 | * 9/1994 | ........ 433/92 |
| WO | WO 95/13030 | 5/1995 | |
| WO | WO 95/14440 | 6/1995 | |

* cited by examiner

*Primary Examiner*—Robert A. Hopkins
(74) *Attorney, Agent, or Firm*—Herbert L. Lerner; Laurence A. Greenberg; Werner H. Stemer

(57) ABSTRACT

A centrifugal separator of vertical axis for the separation of a flowable medium, in particular a dental liquid/solids mixture, from conveying suction air has a motor-driven removal element (10) which is arranged in a flow chamber with a rotationally symmetrical peripheral wall (4) and a bottom limit. A top, central outlet (9) for the suction air and a bottom, peripheral outlet (8) for the flowable medium are flow-connected to an inlet (5) for the mixture to be separated, which opens out between these outlets, the peripheral outlet (8) being surrounded by an annular non-return valve (7). Vanes (16) are provided on the removal element (10) between the mixture inlet (5) and the peripheral outlet (8). The mixture inlet (5) is formed between the bottom edge of the peripheral wall (4) and a holding ring (22) for the non-return valve (7).

19 Claims, 5 Drawing Sheets

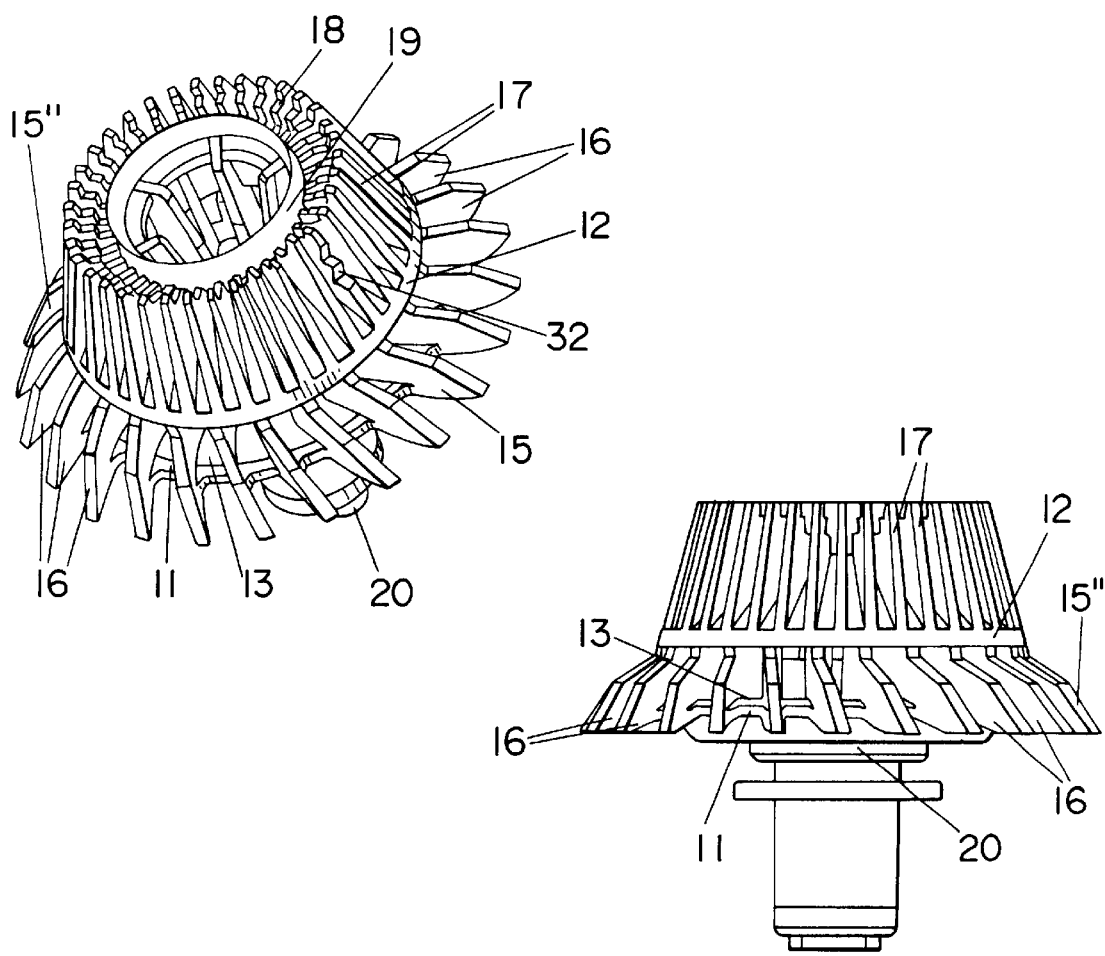

SEPARATOR ELEMENT FOR A CENTRIFUGAL SEPARATOR

Figure 1:
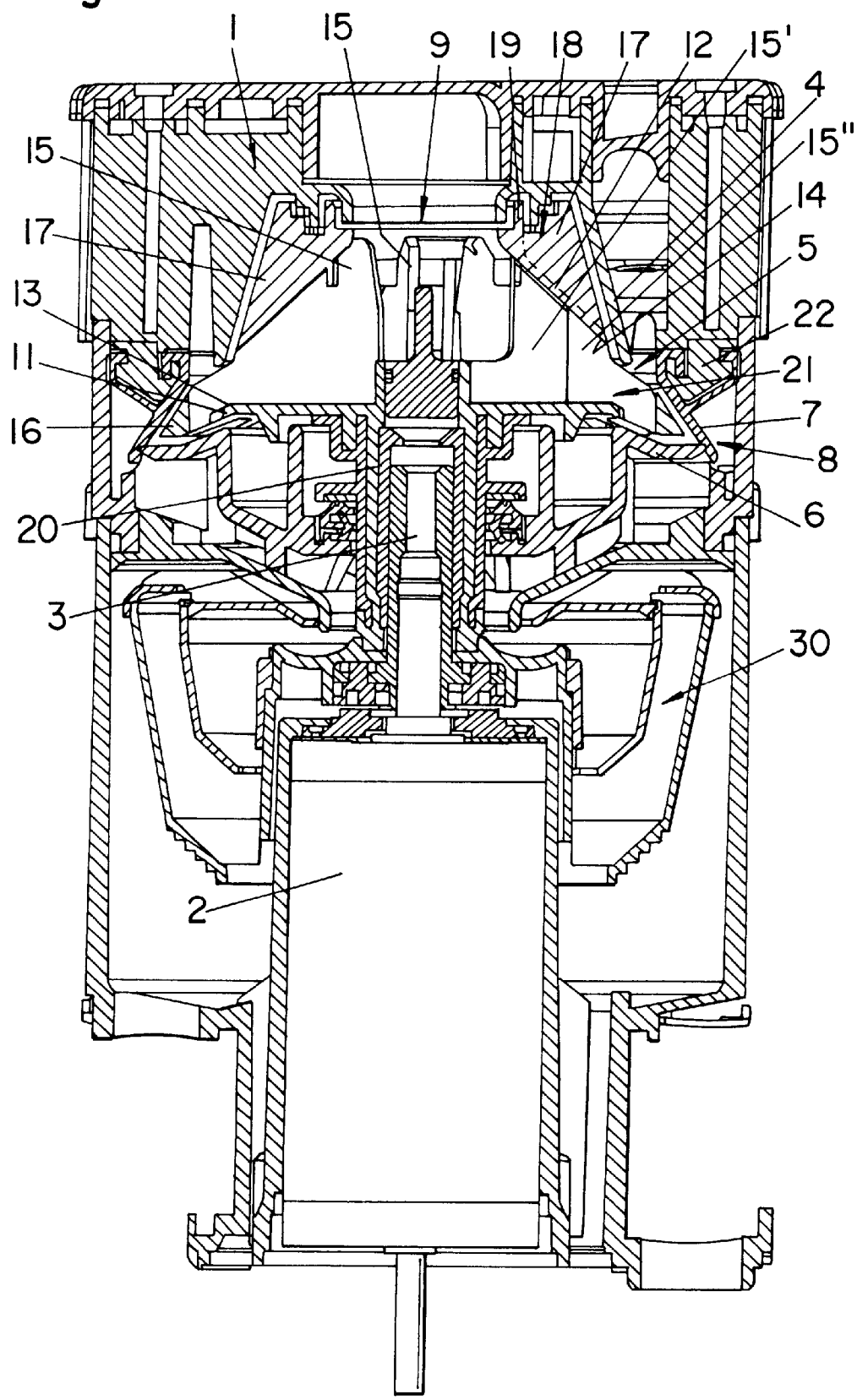

The invention relates to a centrifugal separator of vertical axis for the separation of a flowable medium, in particular a dental liquid/solids mixture, from conveying suction air, having a motor-driven removal element, which is arranged in a flow chamber which has a rotationally symmetrical peripheral wall and a bottom limit, and in which a top, central outlet for the suction air and a bottom, peripheral outlet for the flowable medium are flow-connected to an inlet for the mixture to be separated, which opens out between these two outlets, the peripheral outlet being surrounded by an annular non-return valve, and vanes being provided on the removal element between the mixture inlet and the outlet.

A centrifugal separator of this nature is known, for example, from WO 94/18903. The centrifugal separator has a driven removal element, which essentially forms a pump impeller by means of which the air flow is sucked from the outside inward, i.e. in the opposite direction to the centrifugal forces, over at least one separation edge. The pump impeller has planar, radial vanes which convey the flowable medium outward into the peripheral outlet and force it through the non-return valve. The vanes, which extend all the way to the central outlet for the suction air, also remove residues of the medium from the suction air, so that it enters the outlet which is in communication with an external extraction device in a dry state.

The flow chamber through the removal element is delimited at the top and bottom by rotary parts, the axial distance between which is shortest at the peripheral outlet and becomes greater toward the hub, i.e. as the radius becomes smaller. The surface area of the blades is to be as large as possible, in order, on the one hand, to optimize the separation of the flowable medium from the suction air and, on the other hand, to optimize the way in which it is discharged into the peripheral outlet. However, the number of blades is limited, since the flow chamber must as far as possible not be restricted in the area close to the hub. Although a convex shaping of the base plate does increase the cross section of flow, it forms, since the drive shaft runs vertically, a sump in which residues of the flowable medium accumulate when the removal element is switched off.

The invention is therefore based on the object, in a centrifugal separator of the type described in the introduction, of bringing the mixture which is to be separated into contact with a vane surface area which is as large as possible while neither impairing the flow chamber nor promoting accumulation of residues in the flow chamber.

According to the invention, this is achieved by the fact that the mixture inlet is formed between the bottom edge of the peripheral wall and a holding ring for the non-return valve.

In this way, the mixture inlet, which is preferably annular, is arranged as far as possible toward the outside of the removal element, directly in front of the peripheral outlet, where the peripheral speed of the vanes is correspondingly high. The mixture comes into contact with the removal element from above, and the centrifugal force means that mixture fractions are thrown outward from the vanes and are forced through the outlet and the annular non-return valve. Since the pressure reduction from the suction machine is active at the central outlet for the suction air, the air is diverted inward around the bottom edge of the peripheral wall, entraining mixture fractions. To avoid the accumulation of mixture residues in the removal element when the drive of the removal element is switched off, it is preferable for the bottom limit of the flow chamber to drop down toward the peripheral outlet for the medium below the mixture inlet or for the removal element to be provided with a bottom base plate which has an inner surface which drops down toward the peripheral outlet.

Shaping the bottom limit in this way on the one hand improves the discharge of mixture to the outside but, on the other hand, also reduces the cross-sectional area of the flow chamber, so that, if it is necessary to ensure that no mixture residues can be entrained through the central suction-air outlet, it is necessary to provide sufficient height for the flow chamber, in which the volumes of components which are absolutely necessary are made as small as possible and their surface areas which are active in the separation as large as possible. Therefore, in a further preferred embodiment, the removal element has a hub which is provided only in the lower part of the height of the removal element, and first blades connected to the hub are provided, which first blades are connected to a top guide element and/or to a bottom base plate and the outer ends of which blades form vanes. The shortened hub leaves the central space below the suction-air outlet clear, and the number of first blades connected to the hub is small, for example six. Since, as mentioned, the active surface area inside the removal element is also to be large, in a further preferred embodiment in each case a second blade which is at a radial distance from the hub and the outer end of which forms a further vane is arranged between in each case two first blades which are connected to the hub. The separating effect is improved still further if in each case a third blade, which is at a greater radial distance from the hub and the outer end of which forms a further vane, is arranged between in each case a first blade, which is connected to the hub, and a second blade, which is at a distance from the hub. Therefore, in order, on the one hand, to optimize the separation of the flowable medium from the suction air and, on the other hand, the way in which it is discharged into the peripheral outlet, groups of blades are provided, the group of first blades running through the entire flow chamber from the outside inward, the group of second blades being arranged in the spaces between the first vanes but extending only sufficiently far inward for an adequate passage to remain clear between the first blades, and the additional group of third blades which is preferred being arranged in the peripheral region of the removal element, in each case in the space between a first blade and a second blade. The second and third blades, which are not connected to the hub, are attached to the top guide element and/or to the bottom base plate.

In the abovementioned exemplary embodiment with six first blades, the preferably three groups of blades result in a total of 24 vanes which project into the mixture outlet all the way to the non-return valve.

Figure 2:
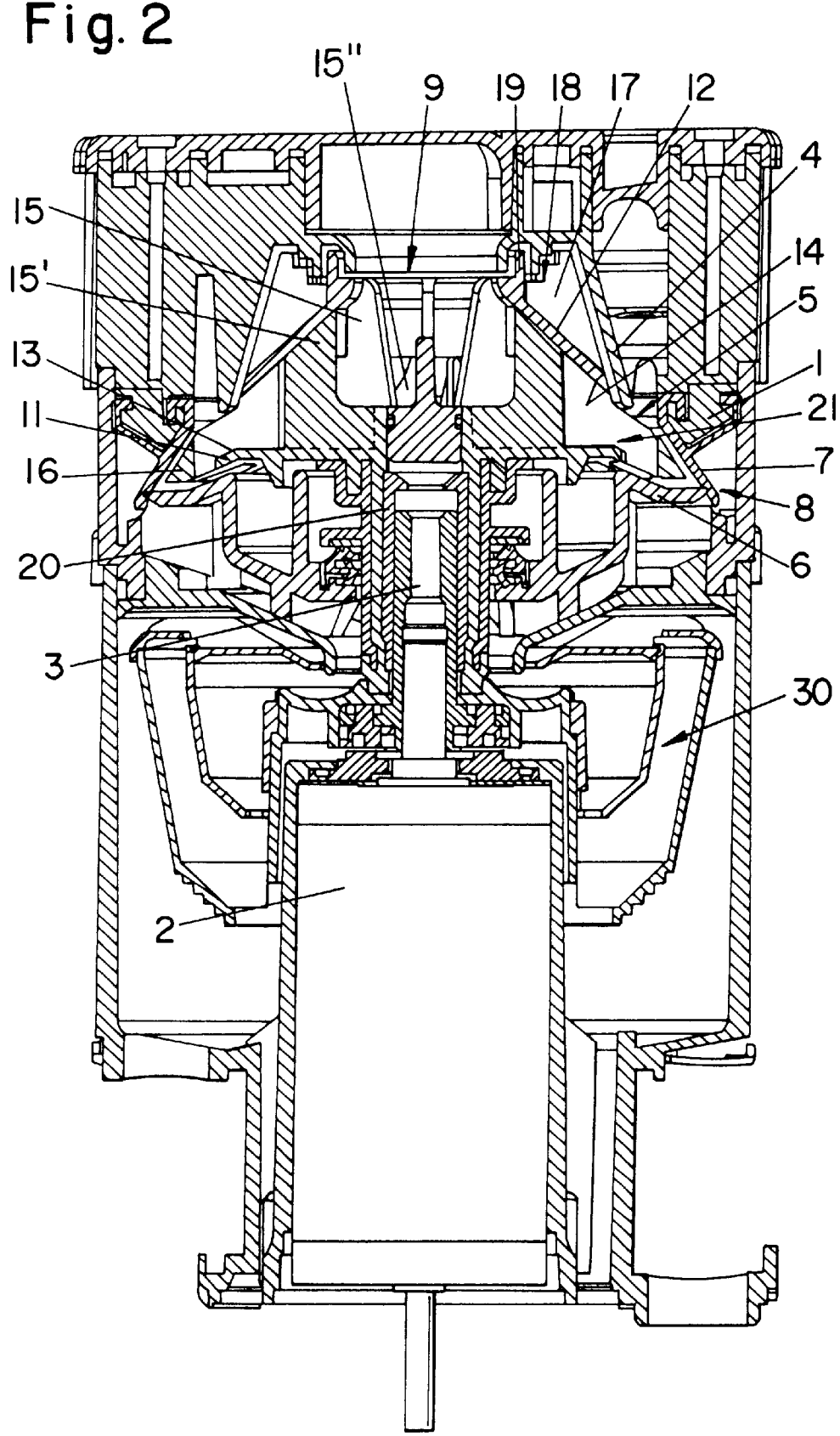
Figure 5:
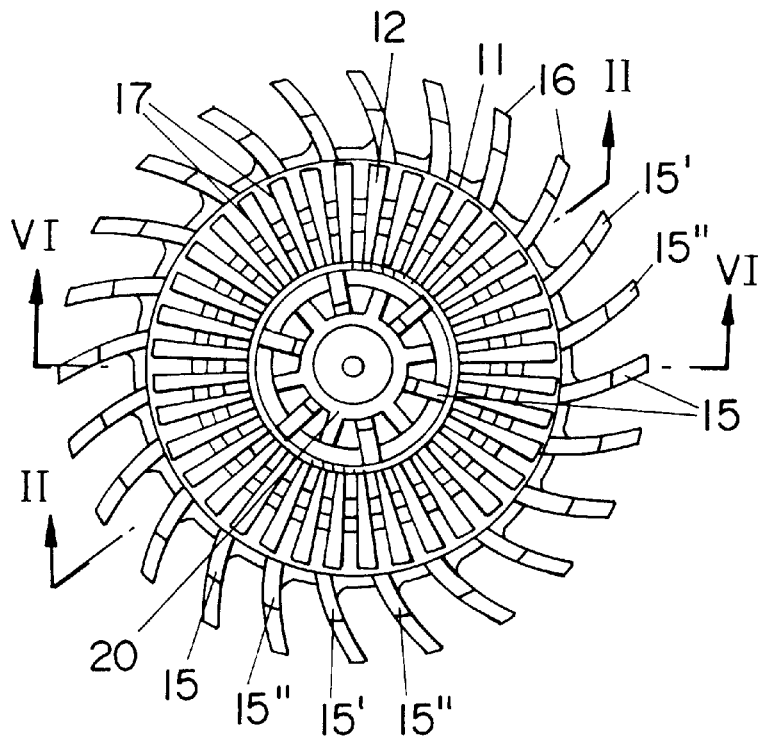
Figure 6:
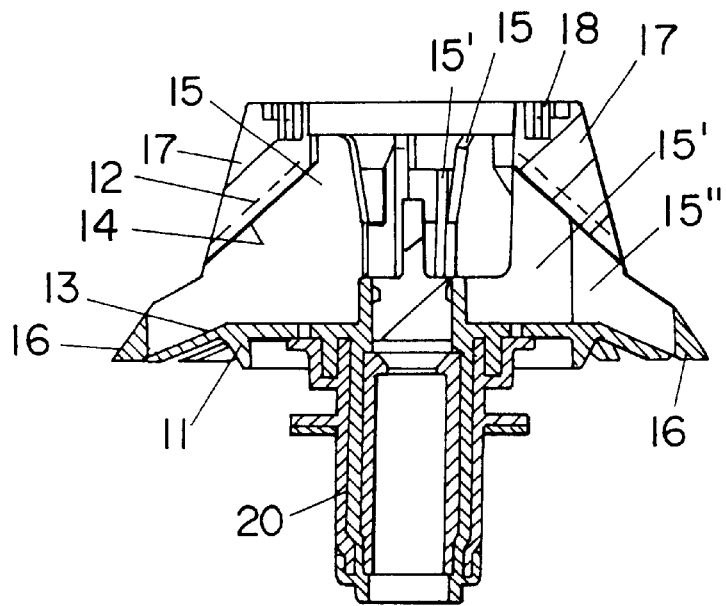
Figure 7:
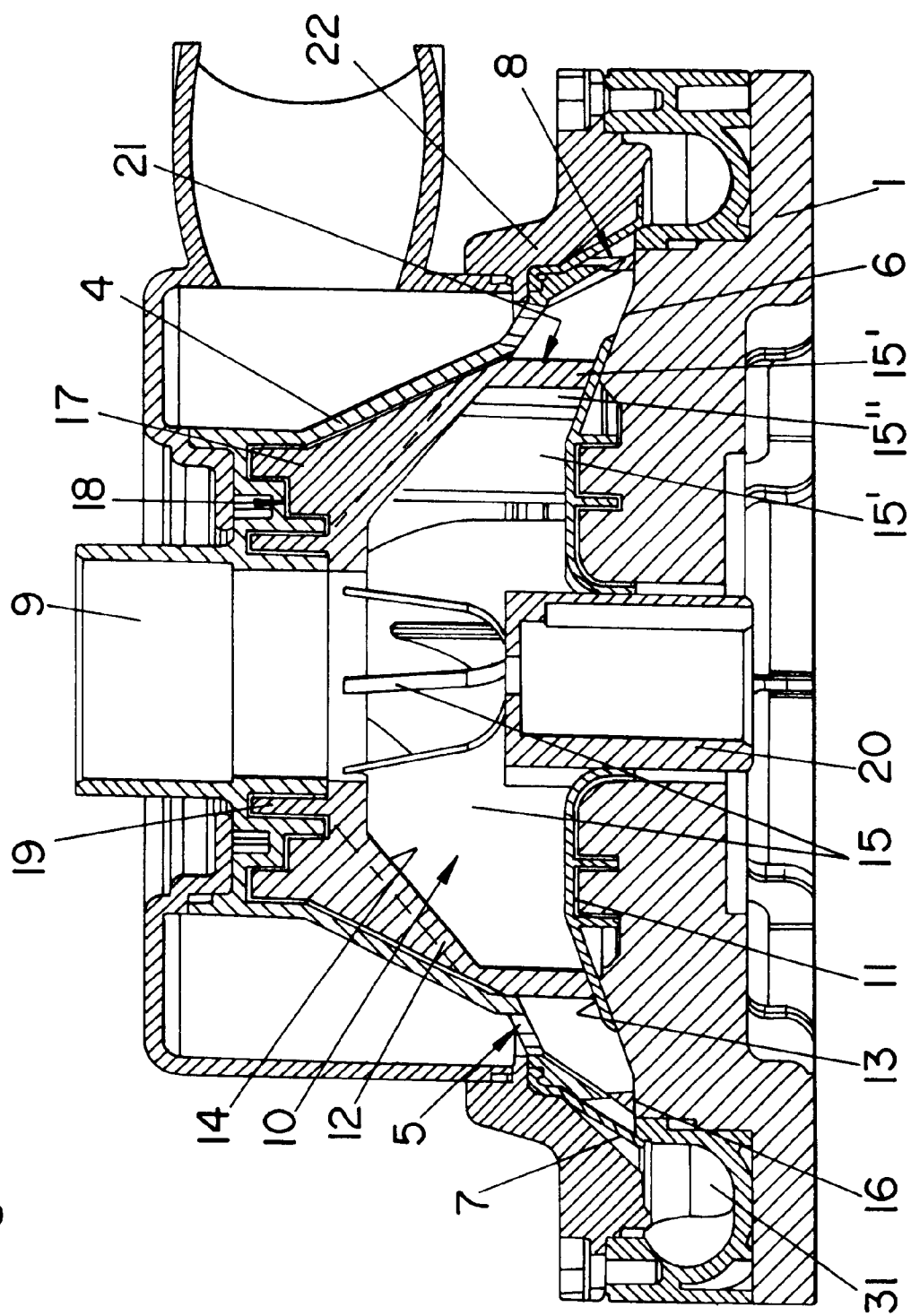

The invention is described in more detail below with reference to the figures in the appended drawing, without being restricted thereto. In the drawing:

FIG. 1 shows an axial section through a first embodiment of a centrifugal separator, in which the removal element is shown in section in accordance with FIG. 6, FIG. 2 shows an axial section through the first embodiment, in which the removal element is in section on line II—II from FIG. 5, FIG. 3 shows a perspective view of the removal element, FIG. 4 shows a plan view from the central outlet, FIG. 5 shows a side view, FIG. 6 show a section on line VI—VI from FIG. 5, and FIG. 7 shows an axial section through a second embodiment of a centrifugal separator.

A centrifugal separator as shown in FIGS. 1 and 2 has a housing 1 which comprises a reduced-pressure region and a normal pressure region. An annular inlet 5 for a mixture of a flowable medium and suction air conveying it, for example for a liquid/solids mixture which is to be sucked out of the mouth of a patient, opens into the reduced-pressure region, the suction air being separated off by means of a removal element 10 which rotates about a vertical axis and being passed, via a central outlet 9, to a reduced-pressure source (not shown), in particular a suction pump. The removal element 10 has a hub 20 which is arranged on the drive shaft 3 of the motor 2, extends over only part of the height of the removal element 10 and from which a plurality of curved first blades 15 project in an axially parallel manner, as well as a bottom base plate 11, the inner surface 13 of which drops down outward, and a top guide element 12, the inner surface 14 of which also drops down outward at a greater angle. The outer edges of the bottom base plate 11 and the top guide element 12, which are relatively close together, delimit an entry gap 21 into the removal element 10 and are assigned to a peripheral outlet 8 for the flowable liquid/solids mixture which has been separated off, which outlet leads from the reduced-pressure region into the normal pressure region and is provided with a non-return valve in the form of a peripheral seal 7 which is pressed against the base 6 of the housing 1, is fixed in a holding ring 22 and is made from elastic material. When the suction pump is working, the peripheral seal 7 is additionally pressed into the closed position by the reduced pressure from this pump. In the outside, normal pressure region, the mixture which has been pressed through the non-return valve flows downward on all sides under the force of gravity, where it is broken down further into solids and liquid, for example by means of a centrifuge 30.

The removal element 10 is arranged in a flow chamber which is delimited by a rotationally symmetrical peripheral wall 4 and the base 6 of the housing 1. A vertical cross-sectional area of the removal element 10 has a length which is derived from the periphery of the removal element 10 and a height which is derived from the axial distance between the peripheral edges of the bottom base plate 11 and the top guide element 12. Since the length of the cross-sectional area shortens with increasing proximity to the axis of rotation, its height increases. In the exemplary embodiment, the inner surface 14 of the top guide elements 12 is a frustoconical surface, the angle of inclination, i.e. the angle of the generatrix to the vertical axis of rotation, being approximately 45°. The inner surface of the bottom base plate 11 is shaped in such a way that it is impossible for residues of the medium to accumulate and, in the exemplary embodiment, comprises an inner annular region which is at right angles to the hub 20 and an inner surface which drops down outward and in which there is likewise a frustoconical surface, but with an angle of inclination which is significantly larger, for example 70°.

First, curved blades 15, which are connected to the base plate 11, project from the hub 20. The active surface area of the first blades 15 decreases toward the outside, since their axial extent, i.e. their height, is progressively decreasing. To increase the active surface area, second blades 15', which extend over only about the outer two thirds of the radius of the removal element 10, are provided between the first blades 15, and in each case third blades 15" are provided only in approximately the outer third of the radius between in each case the first and second blades 15 and 15'. Therefore, the first and second blades 15', 15" are only fixed to the base plate 11.

The ends of all the blades 15, 15', 15" project beyond the peripheries of both the base plate 11 and the guide element 12 and form vanes 16, so that the maximum active vane surface area is provided in the annular space outside the base plate 11 and the guide element 12, into which the annular inlet 5 for the mixture opens, the height of the vane surface area also including the thickness of the base plate 11 and of the top guide element 12. The annular space which is defined by the vanes 16 is delimited at the bottom by the downwardly sloping edge of the housing base 6 and on the outside by the holding ring 22 and the peripheral seal 7 in the peripheral outlet 8. The annular mixture inlet 5 is separated from the flow chamber by a peripheral wall which is fixed to the housing, the bottom edge of the peripheral wall 4 and the holding ring 22 of the peripheral seal 7 delimiting the annular mixture inlet 5. The peripheral wall 4 includes an angle with the outer side of the top guide element 12, so that a chamber which widens upwards is formed, in which substantially triangular sealing vanes 17 with upper shoulders 18 are provided which, together with an annular extension 19 of the top guide element 12, which projects into the central outlet 9, form a gap seal 18 when the removal element 10 is rotating. The sealing vanes 17 discharge any liquid which has penetrated down into the entry gap 21; if appropriate, external notches 32 may be formed, as shown in FIG. 3. The peripheral wall 4 could, at the bottom edge, be provided with an inwardly directed flange, which engages beneath the edge of the inner surface 14, the blades 15, 15', 15" having a suitable recess, and with annular webs which project into the notches 32. For manufacturing engineering reasons, the removal element 10 may be assembled from two parts, of which the bottom part has the hub 20, the base plate 11 and the blades 15, 15', 15", and the top part has the guide element 12 and the sealing vanes 17.

The design shown in FIG. 7, in which neither the motor nor the drive shaft is shown, substantially corresponds to the first design described above. The difference is the structure of the removal element 10, from whose hub 20, which is of low height, curved first blades 15 which are connected to the top guide element 12 once again project. The top guide element 12 also bears the second and third blades 15', 15" and the top sealing vanes 17. In this case, for manufacturing engineering reasons, the base plate 11 with a downwardly sloping edge 13 forms a separate component which is fitted onto the hub 20. A further slight difference from the design shown in FIG. 1 is that an annular channel 31, from which the separated mixture is drained out, is shown outside the peripheral seal 7, which is once again held in a holding ring 22 which delimits the outlet 8 on one side and the annular mixture inlet 5 on the other side.

The sealing vanes 17 between the top guide element 12 and the peripheral wall 4 may also be dispensed with if the two elements are substantially parallel to one another.

What is claimed is:

1. A vertical axis centrifugal separator for the separation of a flowable medium from conveying suction air, comprising:

a housing formed with a flow chamber having a rotationally symmetrical peripheral wall with a lower edge, said flow chamber being formed with an upper, central outlet for suction air, a lower, peripheral outlet for a flowable medium, and an inlet for a mixture to be separated in fluidic communication with and disposed between said upper outlet and said lower outlet;

a motor-driven removal element disposed in said flow chamber, said removal element carrying a plurality of vanes between said mixture inlet and said lower outlet;

an annular check valve surrounding said lower, peripheral outlet, and a holding ring for said check valve;

wherein said mixture inlet is formed between said lower edge of said peripheral wall and said holding ring for said check valve, and a bottom limit of said flow chamber slopes toward said peripheral outlet below said mixture inlet.

2. The centrifugal separator according to claim 1, wherein said removal element has a hub in a lower portion of a height of said removal element, and first blades defining said vanes are connected to at least one of a top guide element and a bottom base plate of said hub are provided, and said first blades form vanes.

3. The centrifugal separator according to claim 2, wherein said top guide element is formed as a hollow frustoconical surface.

4. The centrifugal separator according to claim 3, wherein said hollow frustoconical surface has a generatrix including an angle of at most 45° with a vertical axis.

5. The centrifugal separator according to claim 2, which further comprises second blades at a radial distance from said hub and having an outer end forming a further vane, said second blades being respectively arranged between two first blades connected to said hub.

6. The centrifugal separator according to claim 5, which comprises third blades at a greater radial distance from said hub and having an outer end forming a further vane, said third blades being respectively arranged between a first blade, connected to said hub, and a second blade, disposed at a distance from said hub.

7. The centrifugal separator according to claim 6, wherein said second blades and said third blades are connected to one of said top guide element and said bottom base plate.

8. The centrifugal separator according to claim 3, which comprises a plurality of vanes carried on a top of said top guide element, said vanes having an outer contour approximating said peripheral wall of said flow chamber, and annular projections on the housing and intermeshing extensions of said top guide element in a region of said central outlet for the suction air, said projections and extensions, when said removal element rotates, bringing about dynamic sealing of a gap therebetween.

9. The centrifugal separator according to claim 1, wherein said flow chamber is connected to a dental apparatus to receive therefrom a dental liquid/solids mixture.

10. A vertical axis centrifugal separator for the separation of a flowable medium from conveying suction air, comprising:

a housing formed with a flow chamber having a rotationally symmetrical peripheral wall with a lower edge, said flow chamber being formed with an upper, central outlet for suction air, a lower, peripheral outlet for a flowable medium, and an inlet for a mixture to be separated in fluidic communication with and disposed between said upper outlet and said lower outlet;

a motor-driven removal element disposed in said flow chamber, said removal element including a bottom base plate formed with an inner surface dropping down toward said peripheral outlet and carrying a plurality of vanes between said mixture inlet and said lower, peripheral outlet;

an annular check valve surrounding said lower, peripheral outlet, and a holding ring for said check valve; wherein said mixture inlet is formed between said lower edge of said peripheral wall and said holding ring for said check valve.

11. The centrifugal separator according to claim 10, wherein a plate edge of said base plate lies approximately below a wall edge of said peripheral wall, and said vanes project beyond said plate edge and said wall edge in a radial direction.

12. The centrifugal separator according to claim 10, wherein said removal element has a hub in a lower portion of a height of said removal element, and first blades defining said vanes are connected to at least one of a top guide element and a bottom base plate of said hub are provided, and said first blades form vanes.

13. The centrifugal separator according to claim 12, wherein said top guide element is formed as a hollow frustoconical surface.

14. The centrifugal separator according to claim 13, wherein said hollow frustoconical surface has a generatrix including an angle of at most 45° with a vertical axis.

15. The centrifugal separator according to claim 12, which further comprises second blades at a radial distance from said hub and having an outer end forming a further vane, said second blades being respectively arranged between two first blades connected to said hub.

16. The centrifugal separator according to claim 15, which comprises third blades at a greater radial distance from said hub than said first blades and having an outer end forming a further vane, said third blades being respectively arranged between a first blade, connected to said hub, and a second blade, disposed at a distance from said hub.

17. The centrifugal separator according to claim 15, wherein said second blades and said third blades are connected to one of said top guide element and said bottom base plate.

18. The centrifugal separator according to claim 13, which comprises a plurality of vanes carried on a top of said top guide element, said vanes having an outer contour approximating said peripheral wall of said flow chamber, and annular projections on the housihg and intermeshing extensions of said top guide element in a region of said central outlet for the suction air, said projections and extensions, when said removal element rotates, bringing about dynamic sealing of a gap therebetween.

19. The centrifugal separator according to claim 10, wherein said flow chamber is connected to a dental apparatus to receive therefrom a dental liquid/solids mixture.

* * * * *